(12) United States Patent
Jiang

(10) Patent No.: US 8,469,589 B2
(45) Date of Patent: Jun. 25, 2013

(54) ROTATION MECHANISM FOR X-RAY WALLSTAND HOUSING, X-RAY WALLSTAND HOUSING AND RADIOGRAPHY SYSTEM USING THE SAME

(75) Inventor: Lin Jiang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 237 days.

(21) Appl. No.: 12/952,605

(22) Filed: Nov. 23, 2010

(65) Prior Publication Data

US 2011/0123000 A1    May 26, 2011

(30) Foreign Application Priority Data

Nov. 25, 2009  (CN) .......................... 2009 1 0226585

(51) Int. Cl.
*H01J 31/50* (2006.01)

(52) U.S. Cl.
USPC .......................................... 378/189; 378/208

(58) Field of Classification Search
USPC .............. 378/197, 209, 189, 181, 208; 5/600, 5/601
See application file for complete search history.

(56) References Cited

U.S. PATENT DOCUMENTS

| | | | |
|---|---|---|---|
| 4,802,197 | A | 1/1989 | Juergens |
| 6,609,826 | B1 | 8/2003 | Fujii et al. |
| 6,851,851 | B2 | 2/2005 | Smith et al. |
| 7,798,710 | B1 | 9/2010 | Barnes et al. |
| 2009/0056021 | A1 * | 3/2009 | Kuro et al. .................. 5/601 |

* cited by examiner

*Primary Examiner* — Hoon Song
(74) *Attorney, Agent, or Firm* — Armstrong Teasdale LLP

(57) ABSTRACT

A rotation mechanism for use with an x-ray wallstand housing includes a rotating shaft, a gas spring, a connecting rod, a ball screw nut seat, a ball screw base, a brake, a clutch, a motor, a conveyor belt, a ball screw and a damper disposed between said ball screw base and said ball screw nut seat.

20 Claims, 4 Drawing Sheets

ROTATION MECHANISM FOR X-RAY WALLSTAND HOUSING, X-RAY WALLSTAND HOUSING AND RADIOGRAPHY SYSTEM USING THE SAME

CROSS REFERENCE TO RELATED APPLICATIONS

This application claims the benefit of Chinese Patent Application No. 200910226585.8 filed Nov. 25, 2009, which is hereby incorporated by reference in its entirety.

BACKGROUND OF THE INVENTION

The present invention generally relates to the field of X-ray radiography system, and particularly relates to a rotation mechanism for an x-ray wallstand housing, an x-ray wallstand housing and a radiography system using the same.

X-ray radiography systems existing in the current market are mainly divided into economical-type and non-economical-type radiography systems according to the cost. For a radiography housing of an 0economical-type system, it is generally of fixed type with simple structure, it has no rotation movement and only can perform up-and-down movement, and it is mainly used for taking chest radiograph. According to imaging medium, X-ray radiography systems are mainly divided into three types, i.e. film radiography system, CR (Computerized Radiography, X-ray Computerized Radiography) radiography system and DR (Digital Radiography, X-ray Computerized Radiography) radiography system. CR radiography system is a transitional system between film and digital-medium.

The most widely used radiography system in clinic at present is DR radiography system, which can realize multiple functions on a single system. That is, it is required not only being capable of making up-and-down movement, but also having rotation function, i.e. being capable of shooting an image of e.g. a skull in tilting angle.

As an important component of a multi-function digital radiography system, for example, a chest radiograph stand, can move the radiography housing to different heights and positions for different application demands, and meanwhile can rotate the radiography housing to maintain it at any position of −20° to 90° with respect to a vertical plane.

As shown in FIG. 1, a typical x-ray wallstand housing is illustrated, in mechanical structure, which mainly includes a wallstand column 1, a carriage 2, a radiography housing 3 and a rotation mechanism. Wherein the carriage 2 is mounted on the wallstand column 1 and can make up-and-down movement in vertical direction; the rotation mechanism is positioned on the carriage 2 for driving the radiography housing 3 to position it at any height and angle. In addition, the rotation mechanism also can be integrated together with the carriage 2.

Further, as shown in FIG. 1, the rotation mechanism comprises a rotating shaft 4, a gas spring 5, a ball screw nut seat 7, a connecting rod 6, a ball screw base 12, a brake 16, a clutch 14, a conveyor belt 15, a ball screw 17 and a motor 8, said motor 8 drives said clutch 14 through conveyance by said conveyor belt 15, said clutch 14 is connected with said ball screw 17, said ball screw 17 is connected with said ball screw base 12 and said ball screw nut seat 7, said connecting rod 6 is in parallel with said gas spring 5 and is connected with said ball screw nut seat 7, said brake 16 is positioned on one end of said ball screw 17. The rotation mechanism is mainly used for realizing rotation movement of the radiography housing 3, the support on the rotation mechanism is connected to a rotating bending plate 18, whereby it acts on the rotating bending plate 18, such that the radiography housing 3 fixed on the rotating bending plate 18 rotates about the rotating shaft 4. The gas spring 5 and the upper end of the connecting rod 6 is connected with the upper support of the rotation mechanism in a hinge joint way.

The lower end of the gas spring 5 is connected to the lower support fixed at the rotation mechanism base in a hinge joint way to form two-force bar structure. The gas spring 5 is always used for balancing gravitational torque generated by the weight of the radiography housing 3, the gas spring 5 is similar to a spring, it is compressed when subjected to an external force, and it extends outwards when the external force is reduced to a level at which it is unable to balance the extending force of the gas spring. The variation of the length of the gas spring maintains consistent with the rotating angle of the radiography housing 3, the arm of force of the gas spring (the distance to the rotating shaft center in the direction of the support force) varies with the angle, so the variation of the torque of the support force of the gas spring 5 with the angle can be used to simulate the variation of the gravitational torque of the radiography housing 3 with the angle to achieve an approximately balancing effect. When the radiography housing 3 is rotated closing to 90°, the gravitational torque of the radiography housing 3 gradually draws close to 0 with the variation of the angle, the torque of the support force of the gas spring 5 is also reduced to a minimal value (greater than 0), thus when the radiography housing 3 is rotated closing to 90°, the torque of the support force of the gas spring 5 is greater than the gravitational torque, such that a surplus balancing torque is formed to be an external force rotating the radiography housing 3.

The lower end of the connecting rod 6 is connected with the screw nut seat 7 in a hinge joint way for conveying electrical and manual operation force to realize rotation of the radiography housing 3. The length of the connecting rod 6 maintains the same, the lower end thereof moves horizontally with the screw nut seat 7, the upper end thereof acts on the upper support, makes rotation movement about the rotating shaft 4 together with the radiography housing 3. The torque of the connecting rod 6 varies with the variation of the force applied on the connecting rod 6 and the arm of force thereof (the distance from the axis line of the connecting rod to the rotating axis center).

In FIG. 1 a motor 8 is also comprised which can drive the rotation mechanism to rotate, specifically, it drives the radiography housing 3 to any position and angle through the ball screw nut seat 7 and the connecting rod 6. In addition, the clutch 14 positioned between the motor 8 and the ball screw nut seat 7 can realize manual operation upon the radiography housing 3. The motor 8 is a drive source. The ball screw 17 is of high lead, when it is in free-rotation state, it not only is used for conveying driving force from the motor 8, but also can drive the ball screw 17 through the ball screw nut seat 7 to release force from the connecting rod 6, realizing manual operation. The brake 16 acts on the ball screw 17 and achieves the purpose of braking through the rotation and braking of the ball screw 17. The clutch 14 causes the electrical and manual operation to be respectively independent.

During electrical operation, an electrical button is pressed by hand, the clutch 14, the motor 8 and the brake 16 are simultaneously powered on, the clutch 14 suck, and the brake 16 disengages. The motor 8 rotating drives the ball screw 17 to rotate through the belt 15 and the clutch 14, to drive the ball screw nut to make linear movement, the ball screw nut drives the screw nut seat 7 to rotate the radiography housing 3 about the rotating shaft 4 through the connecting rod 6. The motor 8 is forward and/or reverse to realize the forward and/or reverse rotating direction of the radiography housing 3. During electrical operation, the surplus torque of the gas spring 5 is balanced through the connecting rod 6, electrical control is gradually started and gradually stopped, avoiding the possibility of the radiography housing 3 shooting over 90 degree.

During manual operation, an operator acts on the edge of the radiography housing 3 with one hand, presses a manual switch with the other hand, and assists the rotation movement of the radiography housing 3. When the manual switch is triggered, the motor 8 and the clutch 14 are powered off, the power-down brake 16 is powered on and disengages, the ball screw 17 is separated from the motor drive, the operation force of the operator is applied on the ball screw nut seat 7 through the connecting rod 6, the ball screw 17 of high lead is rotated, whereby manual operation can be realized.

However, when manual operation is performed on the radiography housing 3, the rotation mechanism would have the following problem:

As shown in FIG. 2, because the radiography housing 3 is symmetrical to the rotating shaft 4, in the rotating course of the radiography housing 3, the gravitational torque thereof conforms to the cosine curve. But in the whole course, the gas spring 5 neglects small linear variation in the force value, and simplifies it into constant force. When the radiography housing 3 rotates closing to 90 degree, since there is no force to balance the gas spring 5, the radiography housing 3 will generate a dropping force F. The faster the rotation movement is, the more obvious the dropping is. In other words, when the radiography housing 3 rotates from 0 degree to 90 degree, since the torque of the gas spring 5 exceeds the gravitational torque of the radiography housing 3 when the radiography housing 3 is close to 90 degree, the radiography housing 3 will drop at quick speed and shoot over 90 degree, this will stop under the rotary detent function of the radiography housing 3, the overly quick speed in addition with overshoot will bring about the risk of pinch.

How to solve the problem of drop of the radiography housing 3 during manual operation always troubles those skilled in the art.

BRIEF DESCRIPTION OF THE INVENTION

A technical problem to be solved by the embodiments described herein is to provide a rotation mechanism capable of preventing a radiography housing for an x-ray wallstand housing from dropping, an x-ray wallstand housing and a radiography system using the same.

In order to solve above-mentioned problem, one technical solution is a rotation mechanism for an x-ray wallstand housing including a rotating shaft, a gas spring, a connecting rod, a ball screw nut seat, a ball screw base, a brake, a clutch, a motor, a conveyor belt and a ball screw, said motor drives said clutch through conveyance by said conveyor belt, said clutch is connected with said ball screw, said ball screw is connected with said ball screw base and said ball screw nut seat, said connecting rod is in parallel with said gas spring and is connected with said ball screw nut seat, said brake is positioned at one end of said ball screw, said rotation mechanism further comprises a damper disposed between said ball screw base and said ball screw nut seat.

The greater the speed of force applied on said damper is, the greater the damping force is.

The axis line of said gas spring does not pass through said rotating shaft.

Another technical solution is a x-ray wallstand housing including a wallstand column, a carriage, a radiography housing and a rotation mechanism, said rotation mechanism comprises a rotating shaft, a gas spring, a connecting rod, a ball screw nut seat, a ball screw base, a brake, a clutch, a motor, a conveyor belt and a ball screw, said motor drives said clutch through conveyance by said conveyor belt, said clutch is connected with said ball screw, said ball screw is connected with said ball screw base and said ball screw nut seat, said connecting rod is in parallel with said gas spring and is connected with said ball screw nut seat, said brake is positioned at one end of said ball screw, said rotation mechanism further comprises a damper disposed between said ball screw base and said ball screw nut seat.

The greater the speed of force applied on said damper is, the greater the damping force is.

The axis line of said gas spring does not pass through said rotating shaft.

Yet another technical solution is a X-ray radiography system including an x-ray wallstand housing, said x-ray wallstand housing comprises a wallstand column, a carriage, a radiography housing and a rotation mechanism, said rotation mechanism comprises a rotating shaft, a gas spring, a connecting rod, a ball screw nut seat, a ball screw base, a brake, a clutch, a motor, a conveyor belt and a ball screw, said motor drives said clutch through conveyance by said conveyor belt, said clutch is connected with said ball screw, said ball screw is connected with said ball screw base and said ball screw nut seat, said connecting rod is in parallel with said gas spring and is connected with said ball screw nut seat, said brake is positioned at one end of said ball screw, said rotation mechanism further comprises a damper disposed between said ball screw base and said ball screw nut seat.

The greater the speed of force applied on said damper is, the greater the damping force is.

The axis line of said gas spring does not pass through said rotating shaft.

Compared to the prior art, the beneficial effects of the rotation mechanism for an x-ray wallstand housing, an x-ray wallstand housing and a radiography system using the same are:

First, because a damper is disposed between the ball screw nut seat and the ball screw base, the damper can generate large damping force when the speed of the force applied on it is great, whereby it can well prevent the problem of the radiography housing drop.

Second, because the life period of the damper may achieve 106 times, the reliability of the machine comprising said damper is improved.

In addition, since the operation force has obvious damping sense where the radiography housing draws close to 90 degree during the rotation process of the radiography housing from 0 to 90 degree, operating the radiography housing is more comfortable.

Last, the present invention is simple in mounting, takes little room and has obvious damping function under application conditions.

BRIEF DESCRIPTION OF THE DRAWINGS

In order to understand more thoroughly the present disclosed contents, reference is made to the following description in combination with the figures, in which.

DETAILED DESCRIPTION OF THE INVENTION

Embodiments of the present invention will be described as follows in details, but the present invention is not limited to the following embodiments.

Figure 3:
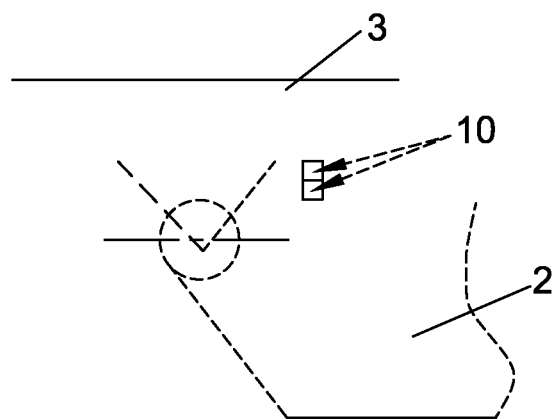
FIG. 3 is a schematic diagram of a rubber detent rotation mechanism for a radiography housing.

One embodiment is as shown in FIG. 3, a rubber detent 10 is disposed between a radiography housing 3 and a carriage 2. Because of the movement of the radiography housing 3, the rubber detent 10 will be compressed from 90° to 91.5°. At the same time, because of such elastic deformation of the rubber detent 10, the radiography housing 3 can be prevented from sudden drop. The elastic deformation range of the rubber detent 10 is approximately 1 mm to 3 mm. Although the application of the rubber detent 10 can prevent the radiography housing 3 from sudden drop, yet there exists bump to the radiography housing 3 which cannot be absorbed.

Figure 4:
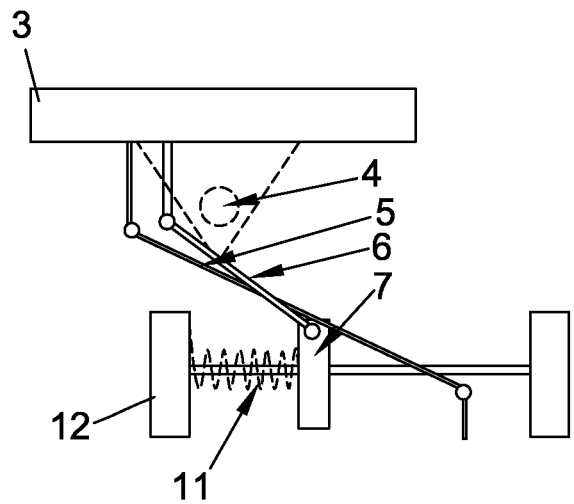
FIG. 4 is a schematic diagram of another spring detent rotation mechanism for a radiography housing.

As shown in FIG. 4, another embodiment includes mounting a rotating damper (not shown) on a rotating shaft 4, and mounting a spring 11 between a ball screw base 12 and a ball screw nut seat 7. However, generally speaking, since the room for mounting the rotating shaft 4 is not larger than approximately 42 mm, the height thereof is not greater than approximately 10.5 mm, and the damping force is not less than approximately 12 N.m (Newton. meter), there is no room on the rotating shaft 4 for mounting the rotating damper.

Figure 1:
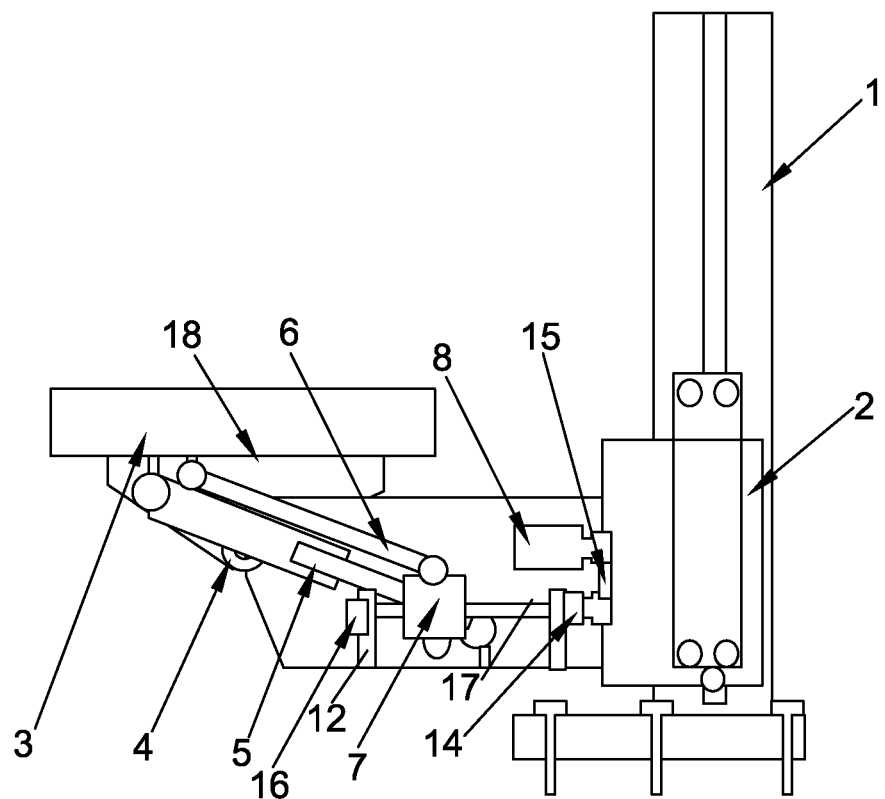
FIG. 1 is a schematic diagram of the structure of a conventional x-ray wallstand housing.
Figure 2:
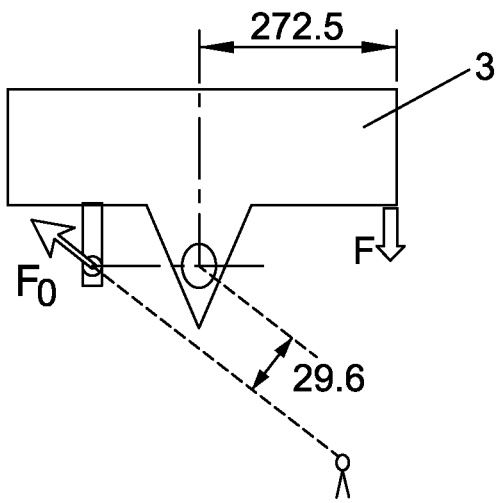
FIG. 2 is a schematic diagram of force applied in rotating a radiography housing by manual operation.
Figure 5:
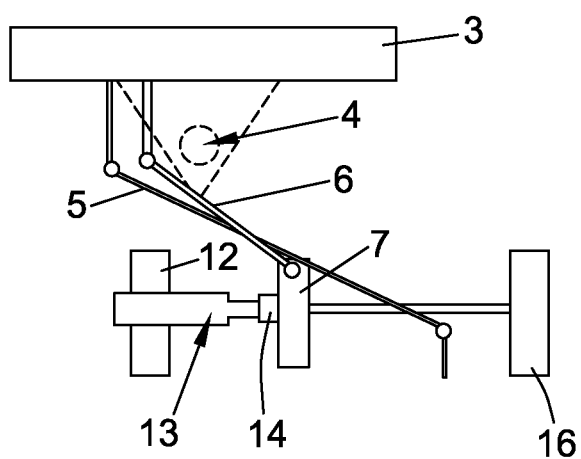
FIG. 5 is a schematic diagram of a rotation mechanism for an x-ray wallstand housing according to the present invention.

FIG. 5 illustrates a schematic diagram of a rotation mechanism for an x-ray wallstand housing according to the present invention. As shown in FIG. 5, said rotation mechanism comprises a rotating shaft 4, a gas spring 5, a connecting rod 6, a ball screw nut seat 7, a ball screw base 12, a brake 16, a clutch 14, a motor 8 (shown in FIG. 1), a conveyor belt 15 (shown in FIG. 1) and a ball screw 17, as well as a damper 13 disposed between said ball screw base 12 and said ball screw nut seat 7.

When the radiography housing 3 is close to 90°, a reacting force generated from sudden compression of the damper 13 forces the radiography housing 3 to maintain at low speed, whereby preventing the radiography box 3 from sudden drop. The reacting force will be augmented non-linearly with speed of the compression. Therefore the rotating operation force required by the radiography housing 3 will not be reduced instantaneously or even be negative. If the ball screw nut seat 7 is at quick speed, the damper 13 generates large damping force while it is compressed at quick speed. The damping force of the damper 13 is related to the speed of the bump object. The quicker the speed at which the damper is bumped, the larger the damping force of the damper 13 is. If the rotating speed of the radiography housing 3 is very low, the damping force of the damper 13 is very small, i.e. approximate to restoring force of the damper 13.

Figure 6:
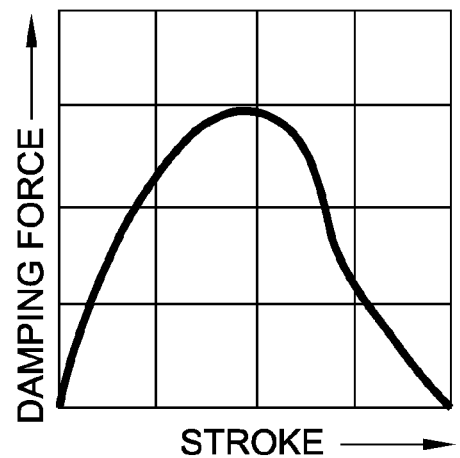
FIG. 6 is a schematic diagram of mechanical properties of a damper in FIG. 5.

As shown in FIG. 6, a schematic diagram of the relation between force applied on the damper 13 and damping force generated by the damper 13 is illustrated. In FIG. 6, the lateral axis represents stroke, the longitudinal axis represents damping force. It can be seen from FIG. 6 that the greater the speed at which a force is applied on the damper 13, the larger the damping force generated by the damper 13 is, in other words, the more energy the damper 13 absorbs; the lower the speed at which a force is applied on the damper 13, the smaller the damping force generated by the damper 13 is.

Figure 7:
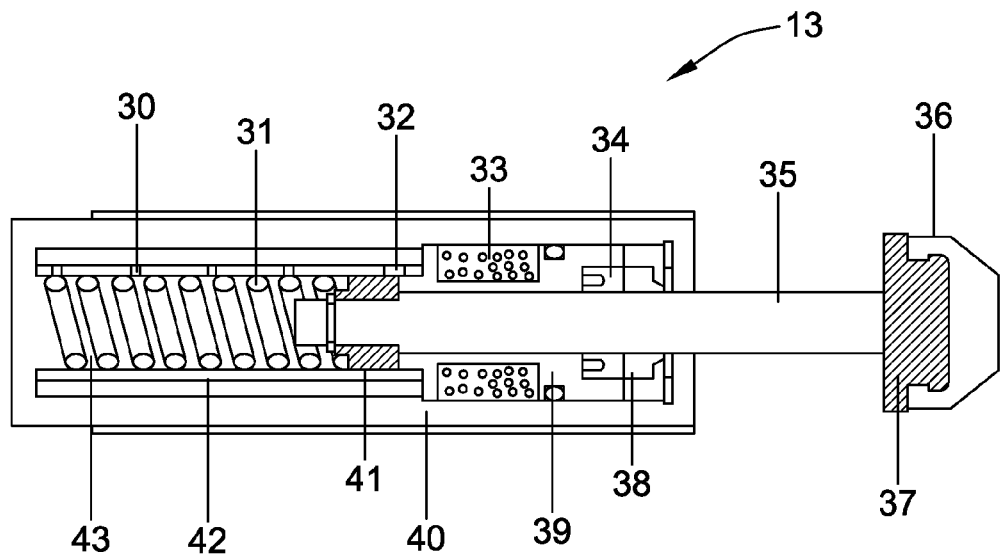
FIG. 7 is an exemplary embodiment of a damper in a rotation mechanism for an x-ray wallstand housing according to the present invention.

As shown in FIG. 7, a schematic diagram of an exemplary embodiment of a damper in a rotation mechanism for an x-ray wallstand housing according to the present invention is illustrated, which is a damper of "Ningbo, China", the greater the speed at which a force is applied on it, the larger damping force it generates. It can be seen from the figure that the damper 13 comprises an oil discharge orifice 30, a spring 31, an oil return orifice 32, a pressure accumulating sponge 33, an oil seal 34, a piston rod 35, a muffle 36, hydraulic oil 43, an inner tube 42, a piston 41, an outer tube 40, a bearing 39, a dustband 38 and a bumped head 37. The working principle thereof is that when the piston rod 35 is shocked, the piston rod 35 drives the piston 41 to extrude the hydraulic oil 43 in the inner tube 42, after the hydraulic oil 43 is compressed, it is discharged from the oil discharge orifice 30 of the inner tube 42, meanwhile, the hydraulic oil 43 discharged from the inner tube 42 refluxes to the inner tube 42 through the oil return orifice 32. If external force is removed, the spring 31 rapidly resets the piston rod 35. The hydraulic oil 43 rapidly returns to the inner tube 42, the damper 13 restores to the initial state and waits for the next action.

The damper 13 of "Ningbo, China" mentioned herein is only an example, it is for the purpose of illustration and is not intended to limit the present invention. Of course, dampers of other types and manufacturers also may be used, any damper 13 with sensitive reaction to the speed of 0.01 m/s is available. In addition, because the room for mounting is limited, it is required that the damper 13 can be mounted into a limited room for mounting. Generally speaking, the room for mounting is generally smaller than approximately 20×20×90 $mm^3$.

As for application of the damper 13 of "Ningbo, China", when the radiography housing 3 is operated manually, if the radiography housing 3 is rotated at quick speed, large damping force generated by the damper 13 will cause the rotation of the radiography housing 3 to be slower. The quicker the speed at which the radiography housing 3 is rotated, the larger the force damping the rotation of the radiography housing 3 by the damper 13 is, the radiography housing 3 will still stops steadily at 90 degree even if it is operated at quick speed, avoiding risk of hand pinch brought forward from fast drop and overshoot of the radiography housing 3. The damper 13 performs a damping function that even cannot be replaced by the spring 11 and the detent block 10. If the rotation operation per se is very slow, that is, the radiography housing 3 is rotated at low speed, because the restoring force of the damper 13 is negligible with respect to the operation force, the rotation per se has small inertia and tends to be steady. Hence the damping force of the damper 13 will cause the operation to be steady and comfortable.

Specifications of some components in the rotation mechanism for an x-ray wallstand housing according to the present invention are given as follows, of course, specifications of some components to be given as follows should not be understood as limitation for the present invention, instead, they are only for the purpose of illustration to facilitate understanding by people.

Assuming that the weight of the radiography housing 3 is 410N (Newton), the weight of the gas spring 5 can be selected to be 370N, its actual force value is simplified to: 3710+1.4 [150−(412−x)]N, wherein x is the mounting length of the gas spring 5 under working state. The ball screw nut seat 7 can adopt the type of 20-20S2, the dynamic load 800 kgf=7840N, the safety factor is 7840/775.73≈10.1.

In this example, the force of the gas spring 5 at 90° is: 370+1.4×(150−147.73)=373. 178N, the surplus torque generated by the gas spring 5 is: 373. 178N×29.873 mm=11147.94636 N·mm, the force generated on the connecting rod 6 is: 11147.94636/35.444=314.5228076N, the force applied on the ball screw nut seat 7 is: 314.5228076 cos 29.27°=274.3662317N≈27.99655426 kgf. A symmetrical design of two dampers 13 may be adopted, each damper 13 is only required to have a damping force of: 27.99655426÷2=13.998≈14 kgf. Therefore when the manual operation speed is greater than 16.33 mm/s, the damping force only needs to reach 14 kgf, thus an adjustable damper 13 may be selected for use, the adjustment range thereof is 1.5~20 kgf. Of course, only one damper 13 may be adopted, it is required to have a damping force of 27.99655426 kgf≈28 kgf.

As for the damper 13, it is usually applied on a machine tool, an automatic production line, and machinery that moves and stops at quick speed, and it is seldom applied on a mechanical product.

Correspondingly, the present invention further discloses an x-ray wallstand housing, comprising a wallstand column 1, a carriage 2, a radiography housing 3 and a rotation mechanism, said rotation mechanism comprises a rotating shaft 4, a gas spring 5, a connecting rod 6, a ball screw nut seat 7, a ball screw base 12, a brake 16, a clutch 14, a motor 8, a conveyor belt 15, a ball screw 17 and a damper 13 disposed between said ball screw base 12 and said ball screw nut seat 7.

The greater the speed of force applied on said damper 13 is, the greater the damping force is. Any damper 13 with sensitive reaction to the speed of 0.01 m/s can be used in the x-ray wallstand housing. Moreover, since the room for mounting is limited, the damper 13 further is required to be mounted in a limited room for mounting. Generally speaking, the room for mounting is smaller than 20×20×90 mm$^3$. The rotation mechanism in the x-ray wallstand housing is similar to the rotation mechanism for an x-ray wallstand housing according to the present invention, so it is not specified herein.

In addition, the present invention further discloses an X-ray radiography system, comprising an x-ray wallstand housing, said x-ray wallstand housing comprises a wallstand column 1, a carriage 2, a radiography housing 3 and a rotation mechanism, said rotation mechanism comprises a rotating shaft 4, a gas spring 5, a connecting rod 6, a ball screw nut seat 7, a ball screw base 12, a brake 16, a clutch 14, a motor 8, a conveyor belt 15, a ball screw 17 and a damper 13 disposed between said ball screw base 12 and said ball screw nut seat 7.

The greater the speed of force applied on said damper 13 is, the greater the damping force of said damper is. Any damper 13 with sensitive reaction to the speed of 0.01 m/s can be used in the chest radiograph stand. Moreover, since the room for mounting is limited, the damper 13 further is required to be mounted in a limited room for mounting. Generally speaking, the room for mounting is smaller than 20×20×90 mm$^3$. The rotation mechanism in the x-ray wallstand housing is similar to the rotation mechanism for an x-ray wallstand housing according to the present invention, so it is not specified herein.

The rotation mechanism for an x-ray wallstand housing of the present invention can be applied into any x-ray wallstand housing and radiography system.

Although the embodiments of the present invention have been described as above in combination with the figures, those skilled in the art can make various variation, amendment or equivalent substitution to the present invention without departing from the scope and spirit of the present invention. Said variation, amendment and equivalent substitution are intended to fall into the spirit and scope limited by the appended claims.

What is claimed is:

1. A rotation mechanism for use with an x-ray wallstand housing, said rotation mechanism comprising a rotating shaft, a gas spring, a connecting rod, a ball screw nut seat, a ball screw base, a brake, a clutch, a motor, a conveyor belt, a damper, and a ball screw, said motor configured to drive said clutch through conveyance by said conveyor belt, said clutch coupled to said ball screw, said ball screw coupled to said ball screw base and said ball screw nut seat, said connecting rod positioned in parallel with said gas spring and coupled to said ball screw nut seat, said brake positioned at one end of said ball screw, said damper disposed between said ball screw base and said ball screw nut seat.

2. A rotation mechanism for an x-ray wallstand housing according to claim 1, wherein the greater the speed of force applied on said damper, the greater the damping force.

3. A rotation mechanism for an x-ray wallstand housing according to claim 2, wherein an axis line of said gas spring does not pass through said rotating shaft.

4. An x-ray wallstand housing, comprising:
   a wallstand column;
   a carriage;
   a radiography housing; and
   a rotation mechanism comprising a rotating shaft, a gas spring, a connecting rod, a ball screw nut seat, a ball screw base, a brake, a clutch, a motor, a conveyor belt, a damper and a ball screw, said motor configured to drive said clutch through conveyance by said conveyor belt, said clutch coupled to said ball screw, said ball screw coupled to said ball screw base and said ball screw nut seat, said connecting rod positioned in parallel with said gas spring and coupled to said ball screw nut seat, said brake positioned at one end of said ball screw, said damper disposed between said ball screw base and said ball screw nut seat.

5. An x-ray wallstand housing according to claim 4, wherein the greater the speed of force applied on said damper, the greater the damping force.

6. An x-ray wallstand housing according to claim 5, wherein an axis line of said gas spring does not pass through said rotating shaft.

7. A radiography system comprising a chest radiograph stand, said chest radiograph stand comprising:
   a wallstand column;
   a carriage;
   a radiography housing; and
   a rotation mechanism comprising a rotating shaft, a gas spring, a connecting rod, a ball screw nut seat, a ball screw base, a brake, a clutch, a motor, a conveyor belt, a damper, and a ball screw, said motor configured to drive said clutch through conveyance by said conveyor belt, said clutch coupled to said ball screw, said ball screw coupled to said ball screw base and said ball screw nut seat, said connecting rod positioned in parallel with said gas spring and coupled to said ball screw nut seat, said brake positioned at one end of said ball screw, said damper disposed between said ball screw base and said ball screw nut seat.

8. A radiography system according to claim 7, wherein the greater the speed of force applied on said damper, the greater the damping force.

9. A radiography system according to claim 8, wherein an axis line of said gas spring does not pass through said rotating shaft.

10. A rotation mechanism for an x-ray wallstand housing according to claim 1, further comprising a carriage.

11. An x-ray wallstand housing according to claim 4, wherein said carriage is configured to move along said wallstand column to position said radiography housing.

12. An x-ray wallstand housing according to claim 4, wherein said rotation mechanism is configured to position said radiography housing at at least one of a desired height and a desired angle.

13. An x-ray wallstand housing according to claim 4, wherein said rotation mechanism comprises said carriage.

14. An x-ray wallstand housing according to claim 4, further comprising a rotating bending plate coupled to said radiography housing, said rotation mechanism configured to cause said rotating bending plate to rotate about a shaft.

15. An x-ray wallstand housing according to claim 4, wherein said gas spring and an upper end of said connecting rod are hingedly coupled to said rotating mechanism.

16. A radiography system according to claim 7, wherein said carriage is configured to move along said wallstand column to position said radiography housing.

17. A radiography system according to claim 7, wherein said rotation mechanism is configured to position said radiography housing at at least one of a desired height and a desired angle.

18. A radiography system according to claim 7, wherein said rotation mechanism comprises said carriage.

19. A radiography system according to claim 7, further comprising a rotating bending plate coupled to said radiography housing, said rotation mechanism configured to cause said rotating bending plate to rotate about a shaft.

20. A radiography system according to claim 7, wherein said gas spring and an upper end of said connecting rod are hingedly coupled to said rotating mechanism.

* * * * *